(12) United States Patent
Chapman

(10) Patent No.: US 7,105,002 B2
(45) Date of Patent: Sep. 12, 2006

(54) ANASTOMOSIS DEVICE AND METHOD

(75) Inventor: Troy J. Chapman, Palo Alto, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/766,170

(22) Filed: Jan. 19, 2001

(65) Prior Publication Data

US 2001/0001827 A1    May 24, 2001

Related U.S. Application Data

(63) Continuation of application No. 09/037,109, filed on Mar. 9, 1998, now Pat. No. 6,176,864.

(51) Int. Cl.
*A61B 17/08* (2006.01)

(52) U.S. Cl. .................................. 606/153

(58) Field of Classification Search ............... 606/151, 606/153; 623/1.13, 1.14, 1.25, 1.23, 1.35, 623/1.36
See application file for complete search history.

(56) References Cited

U.S. PATENT DOCUMENTS

| | | |
|---|---|---|
| 3,254,650 A | 6/1966 | Collito |
| 3,254,651 A | 6/1966 | Collito |
| 3,519,187 A | 7/1970 | Kapitanov et al. |
| 3,561,448 A | 2/1971 | Peternel |
| 3,657,744 A | 4/1972 | Ersek |
| 3,683,926 A | 8/1972 | Suzuki |
| 3,774,615 A | 11/1973 | Lim et al. |
| 3,805,793 A | 4/1974 | Wright |
| 4,130,904 A * | 12/1978 | Whalen ............ 138/122 |
| 4,350,160 A | 9/1982 | Kolesov et al. |
| 4,352,358 A | 10/1982 | Angelchik |
| 4,366,819 A * | 1/1983 | Kaster ............ 606/153 |
| 4,368,736 A * | 1/1983 | Kaster ............ 606/153 |
| 4,485,816 A | 12/1984 | Krumme |
| 4,503,569 A | 3/1985 | Dotter |
| 4,523,592 A | 6/1985 | Daniel |
| 4,553,542 A | 11/1985 | Schenck et al. |
| 4,592,754 A | 6/1986 | Gupte et al. |
| 4,593,693 A | 6/1986 | Schenck |
| 4,607,637 A | 8/1986 | Berggren et al. |
| 4,617,932 A | 10/1986 | Kornberg |
| 4,624,255 A | 11/1986 | Schenck et al. |
| 4,624,257 A | 11/1986 | Berggren et al. |

(Continued)

FOREIGN PATENT DOCUMENTS

DE    24 50 877    5/1975

(Continued)

*Primary Examiner*—Eduardo C. Robert
*Assistant Examiner*—D. Jacob Davis
(74) *Attorney, Agent, or Firm*—Brian Tomko

(57) ABSTRACT

An anastomosis device for use in coupling an end of a graft vessel to a side of a target vessel. The target vessel has an opening formed in a side wall thereof for insertion of the device. The device comprises a tubular member, at least a portion thereof being radially compressible to a compressed state for insertion of the tubular member into the opening in the target vessel and expandable from the compressed state to an expanded state for engagement of an inner graft vessel surface with an inner surface of the target vessel after insertion of the tubular member into the opening in the side wall of the target vessel. The compressible portion of the tubular member has an inner surface and an outer surface defining a wall thickness therebetween. The wall thickness of the compressible portion in its compressed state is less than the wall thickness of the compressible portion in its expanded state.

21 Claims, 10 Drawing Sheets

U.S. PATENT DOCUMENTS

| | | |
|---|---|---|
| 4,657,019 A | 4/1987 | Walsh et al. |
| 4,665,906 A | 5/1987 | Jervis |
| 4,712,551 A | 12/1987 | Rayhanabad |
| 4,733,665 A | 3/1988 | Palmaz |
| 4,747,407 A | 5/1988 | Liu et al. |
| 4,776,337 A | 10/1988 | Palmaz |
| 4,787,386 A | 11/1988 | Walsh et al. |
| 4,873,975 A | 10/1989 | Walsh et al. |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,917,114 A | 4/1990 | Green et al. |
| 5,002,563 A | 3/1991 | Pyka et al. |
| 5,100,429 A | 3/1992 | Sinofsky et al. |
| 5,104,399 A | 4/1992 | Lazarus |
| 5,119,983 A | 6/1992 | Green et al. |
| 5,122,156 A | 6/1992 | Granger et al. |
| 5,197,978 A | 3/1993 | Hess |
| 5,207,695 A | 5/1993 | Trout, III |
| 5,211,658 A | 5/1993 | Clouse |
| 5,211,683 A | 5/1993 | Maginot |
| 5,213,580 A | 5/1993 | Slepian et al. |
| 5,246,452 A * | 9/1993 | Sinnott ................. 623/1.23 |
| 5,254,130 A | 10/1993 | Poncet et al. |
| 5,275,622 A | 1/1994 | Lazarus et al. |
| 5,304,220 A | 4/1994 | Maginot |
| 5,316,023 A | 5/1994 | Palmaz et al. |
| 5,323,789 A * | 6/1994 | Berggren et al. ........... 128/898 |
| 5,328,471 A | 7/1994 | Slepian |
| 5,336,233 A | 8/1994 | Chen |
| 5,366,462 A | 11/1994 | Kaster et al. |
| 5,387,235 A | 2/1995 | Chuter |
| 5,397,345 A | 3/1995 | Lazarus |
| 5,397,355 A | 3/1995 | Marin et al. |
| 5,443,497 A | 8/1995 | Venbrux |
| 5,452,733 A | 9/1995 | Sterman et al. |
| 5,456,712 A | 10/1995 | Maginot |
| 5,478,354 A | 12/1995 | Tovey et al. |
| 5,486,183 A | 1/1996 | Middleman et al. |
| 5,503,635 A | 4/1996 | Sauer et al. |
| 5,507,769 A | 4/1996 | Marin et al. |
| 5,522,834 A | 6/1996 | Fonger et al. |
| 5,522,880 A | 6/1996 | Barone et al. |
| 5,522,881 A | 6/1996 | Lentz |
| 5,545,214 A | 8/1996 | Stevens |
| 5,562,690 A | 10/1996 | Green et al. |
| 5,575,815 A | 11/1996 | Slepian et al. |
| 5,601,572 A | 2/1997 | Middleman et al. |
| 5,662,609 A | 9/1997 | Slepian |
| 5,662,712 A | 9/1997 | Pathak et al. |
| 5,665,063 A | 9/1997 | Roth et al. |
| 5,670,161 A * | 9/1997 | Healy et al. ............. 623/1.42 |
| 5,674,287 A | 10/1997 | Slepian et al. |
| 5,695,504 A | 12/1997 | Gifford, III et al. |
| 5,698,189 A | 12/1997 | Rowe et al. |
| 5,723,004 A * | 3/1998 | Dereume et al. .......... 623/1.35 |
| 5,755,778 A | 5/1998 | Kleshinski |
| 5,769,870 A | 6/1998 | Salahieh et al. |
| 5,797,920 A | 8/1998 | Kim |
| 5,820,628 A | 10/1998 | Middleman et al. |
| 5,824,040 A * | 10/1998 | Cox et al. ................. 623/1.35 |
| 5,830,222 A | 11/1998 | Makower |
| 5,830,229 A * | 11/1998 | Konya et al. .............. 606/198 |
| 5,843,166 A * | 12/1998 | Lentz et al. .............. 623/1.13 |
| 5,881,943 A | 3/1999 | Heck et al. |
| 5,899,935 A | 5/1999 | Ding |
| 5,902,332 A | 5/1999 | Schatz |
| 5,904,697 A * | 5/1999 | Gifford et al. ............. 606/153 |
| 5,925,054 A * | 7/1999 | Taylor et al. .............. 606/108 |
| 5,972,017 A | 10/1999 | Berg et al. |
| 5,976,159 A | 11/1999 | Bolduc et al. |
| 5,976,178 A | 11/1999 | Goldsteen et al. |
| 6,019,788 A * | 2/2000 | Butters et al. ................. 604/8 |
| 6,030,395 A * | 2/2000 | Nash et al. ................. 606/153 |
| 6,036,702 A | 3/2000 | Bachinski |
| 6,074,416 A | 6/2000 | Berg et al. |
| 6,120,432 A | 9/2000 | Sullivan et al. |
| 6,123,714 A * | 9/2000 | Gia et al. ...................... 606/1 |
| 6,190,353 B1 | 2/2001 | Makower et al. |
| 6,206,912 B1 | 3/2001 | Goldsteen et al. |
| 6,210,430 B1 | 4/2001 | Solem |
| 6,280,467 B1* | 8/2001 | Leonhardt .................. 623/1.16 |
| 6,283,991 B1* | 9/2001 | Cox et al. .................. 623/1.13 |
| 6,302,905 B1 | 10/2001 | Goldsteen et al. |
| 6,330,965 B1 | 12/2001 | Milliman |
| 6,391,036 B1 | 5/2002 | Berg et al. |
| 6,447,540 B1* | 9/2002 | Fontaine et al. ........... 623/1.12 |
| 6,451,048 B1 | 9/2002 | Berg et al. |
| 6,461,320 B1 | 10/2002 | Yencho et al. |
| 6,485,496 B1 | 11/2002 | Suyker et al. |
| 6,613,611 B1 | 9/2003 | How et al. |
| 6,616,675 B1 | 9/2003 | Evard et al. |
| 6,702,829 B1 | 3/2004 | Bachinski et al. |
| 2001/0041927 A1 | 11/2001 | Solem |

FOREIGN PATENT DOCUMENTS

| | | |
|---|---|---|
| EP | 0 791 332 A1 | 8/1997 |
| WO | WO 96/25897 | 8/1996 |
| WO | WO 97/28745 | 8/1997 |
| WO | WO 98/19608 | 5/1998 |
| WO | WO 98/19618 | 5/1998 |
| WO | WO 98/19629 | 5/1998 |
| WO | WO 98/19630 | 5/1998 |
| WO | WO 98/19631 | 5/1998 |
| WO | WO 98/19632 | 5/1998 |
| WO | WO 98/19634 | 5/1998 |
| WO | WO 98/19636 | 5/1998 |
| WO | WO 98/55027 | 12/1998 |
| WO | 99/21491 | * 5/1999 |

* cited by examiner

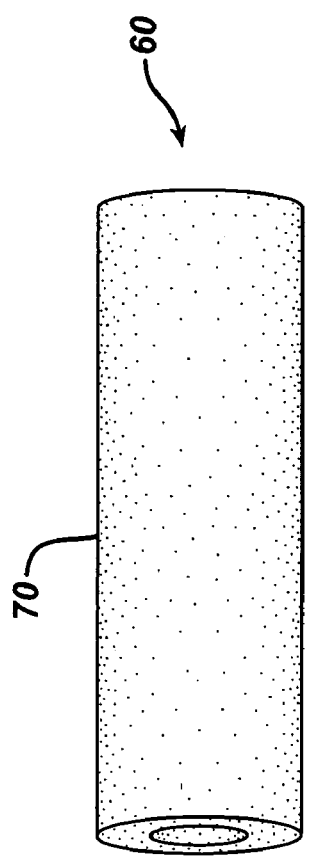
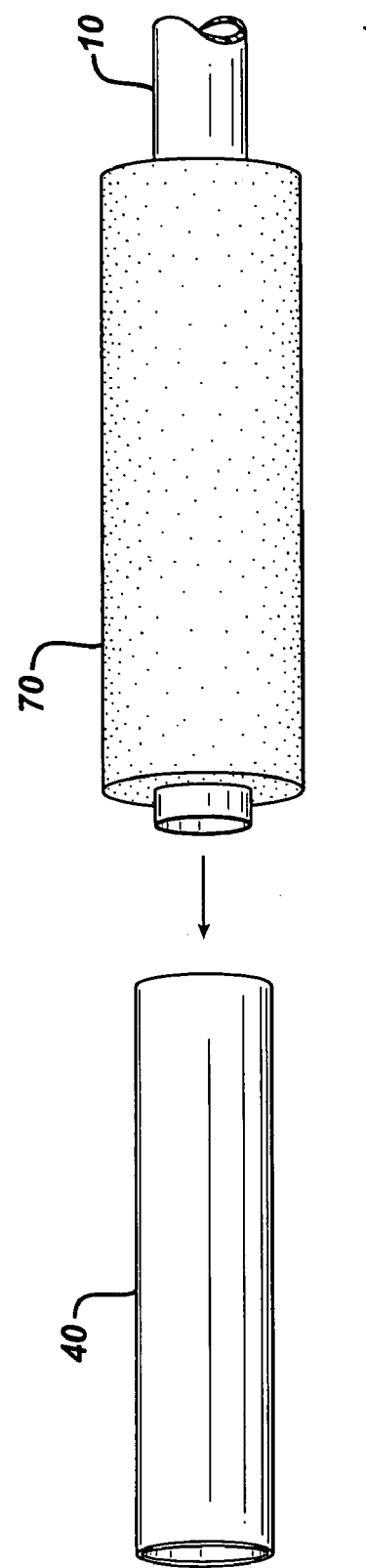

ANASTOMOSIS DEVICE AND METHOD

This application is a continuation of Ser. No. 09/037,109 filed on Mar. 9, 1998, now U.S. Pat. No. 6,176,864.

FIELD OF THE INVENTION

The present invention relates generally to medical devices and methods for performing a vascular anastomosis and, more particularly, to preferred devices and methods for sealingly joining a graft vessel, such as a coronary bypass graft, to the side wall of a target vessel, such as a coronary artery, in an anastomosis.

BACKGROUND OF THE INVENTION

A manifestation of coronary artery disease is the build-up of plaque on the inner walls of the coronary arteries, which causes narrowing or complete closure of these arteries, resulting in insufficient blood flow. This deprives the heart muscle of oxygen and nutrients, leading to ischemia, possible myocardial infarction, and even death. Surgery to alleviate this problem often involves creating an anastomosis between a coronary artery and a graft vessel to restore a blood flow path to essential tissues. An anastomosis is a surgical procedure by which two vascular structures, such as a graft vessel and a coronary artery, are interconnected.

Current methods available for creating an anastomosis include hand suturing the vessels together. Connection of interrupted vessels with stitches has inherent drawbacks. For example, it is difficult to perform and requires great skill and experience on the part of the surgeon due in large part to the extremely small scale of the vessels. For example, the coronary arteries typically have a diameter in the range of between about 1 to 5 mm, and the graft vessels have a diameter on the order of about 1 to 4 mm for an arterial graft such as a mammary artery, or about 4 to 8 mm for a vein graft such as a saphenous vein. Other drawbacks of connection with stitches are the long duration of the operation, during which period in conventional open-heart coronary artery bypass graft (CABG) surgery the heart is arrested and the patient is maintained under cardioplegic arrest and cardiopulmonary bypass. Cardiopulmonary bypass has been shown to be the cause of many of the complications that have been reported in conventional CABG, such as stroke. The period of cardiopulmonary bypass should be minimized, if not avoided altogether, to reduce patient morbidity.

One approach to coronary artery bypass grafting that avoids cardiopulmonary bypass is performing the suturing procedure on a beating heart. At present, however, safe, reproducible, and precise anastomosis between a stenotic coronary artery and a bypass graft vessel presents numerous obstacles including continuous cardiac translational motion which makes meticulous microsurgical placement of graft sutures extremely difficult. The constant translational motion of the heart and bleeding from the opening in the coronary artery hinder precise suture placement in the often tiny coronary vessel.

The above mentioned drawbacks of hand suturing have led to the development of various approaches to stitchless vascular connection or anastomosis which has the advantage of quick and simple execution and undamaged vascular endothelium. Some approaches to stitchless anastomosis used rigid rings prepared from various materials. For example, Geotz et al., INTERNAL MAMMARY-CORONARY ARTERY ANASTOMOSIS—A Nonsuture Method Employing Tantalum Rings, J. Thoracic and Cardiovasc. Surg. Vol. 41 No. 3, 1961, pp. 378–386, discloses a method for joining blood vessels together using polished siliconized tantalum rings which are circumferentially grooved. The free end of the internal mammary is passed through a ring chosen according to the size of the stenotic coronary artery. The free end of the mammary artery is everted over one end of the ring as a cuff and fixed with a silk ligature which is tied around the most proximal of the circular grooves in the ring. The cuffed internal mammary artery is inserted into an incision in the target coronary artery. The ring is fixed in place and sealingly joined to the target coronary artery by tying one or more sutures circumferentially around the target vessel and into one or more circular grooves in the ring. An intimal-to-intimal anastomosis results and dissection of blood between the coronary artery and the cuffed internal mammary artery is largely prevented.

The use of metallic coupling rings is also disclosed in Carter et al., Direct Nonsuture Coronary Artery Anastomosis in the Dog, Annals of Surgery, Volume 148, No. 2, 1958, pp. 212–218 (describing use of rigid polyethylene rings for stitchless vascular connections). Moreover, for example, U.S. Pat. No. 4,624,257 to Berggren et al. describes a device consisting of a pair of rigid rings each having a central opening through which the end of the coronary or graft vessel is drawn and everted over the rings. A set of sharp pins extends outwardly from the face of each ring and pierce through the vessel wall in the everted configuration. The rings are then joined together to align the end of the graft vessel with the opening in the target vessel.

However, no permanently satisfactory results have been reported with the use of rigid rings. A rigid ring presents a foreign body of relatively heavy weight which does not heal well and produces pressure necrosis. Moreover, the use of rigid rings that completely encircle the graft vessel and the arteriotomy creates a severe "compliance mismatch" relative to both the coronary artery and the graft vessel at the anastomosis site which could lead to thrombosis. That is, recent studies suggest that the anastomosis site should not be dramatically different in compliance relative to either the coronary artery or the vascular graft, which is the case when using rigid rings to sealingly join two vessels together.

Another method currently available for stitchless anastomosis involves the use of stapling devices. These instruments are not easily adaptable for use in vascular anastomosis. It is often difficult to manipulate these devices through the vessels without inadvertently piercing a side wall of the vessel. Moreover, as noted above, the scale of the vessels is extremely small, and it is extremely difficult to construct a stapling device that can work reliably on such a small scale to provide a consistent and precise leak-free vascular anastomosis.

SUMMARY OF THE INVENTION

The present invention involves improvements to devices and methods for performing vascular anastomoses. The invention facilitates positioning one vessel in the fluid path of another vessel to enhance the fluid flow juncture therebetween. In one aspect of the invention, a graft vessel, such as an internal mammary artery, is sealingly joined to a target vessel, such as a left anterior descending artery. The present invention eliminates the need for meticulous suturing and may reduce the amount of time required to make an anastomosis, while still providing a substantially safe, leak-free anastomosis.

In one aspect of the present invention, an anastomosis device generally comprises a tubular member. At least a portion of the tubular member is radially compressible to a compressed state for insertion of the tubular member into an opening formed in a target vessel and expandable from the compressed state to an expanded state for engagement of the graft vessel with an inner surface of the target vessel after insertion of the tubular member into the opening in the side wall of the target vessel. The compressible portion of the tubular member has an inner surface and an outer surface defining a wall thickness therebetween. The wall thickness of the compressible portion in its compressed state is less than the wall thickness of the compressible portion in its expanded state.

A method of the present invention generally comprises the steps of providing a graft vessel with a fastener coupled thereto, the fastener comprising a radially compressible portion; exerting an inwardly directed radial force over at least a portion of the compressible portion until the compressible portion has an outer diameter smaller than the diameter of an opening formed in a side wall of the target vessel; inserting at least a portion of the fastener into the opening in the side wall of the target vessel; and removing the radial force to allow the compressible portion of the fastener to radially expand to sealingly engage the graft vessel with an inner wall of the target vessel.

The above is a brief description of some deficiencies in the prior art and advantages of the present invention. Other features, advantages, and embodiments of the invention will be apparent to those skilled in the art from the following description, accompanying drawings and claims.

BRIEF DESCRIPTION OF THE DRAWINGS

FIG. 1A is a cross-sectional view of the anastomosis device of FIG. 1 taken through the line A—A of FIG. 1.

FIG. 10 is an alternative embodiment of the anastomosis device of FIG. 1.

FIG. 11 shows the anastomosis device of FIG. 10 with a graft vessel inserted therein prior to insertion of the device into an opening in the tubular introducer.

DESCRIPTION OF THE INVENTION

Figure 1:
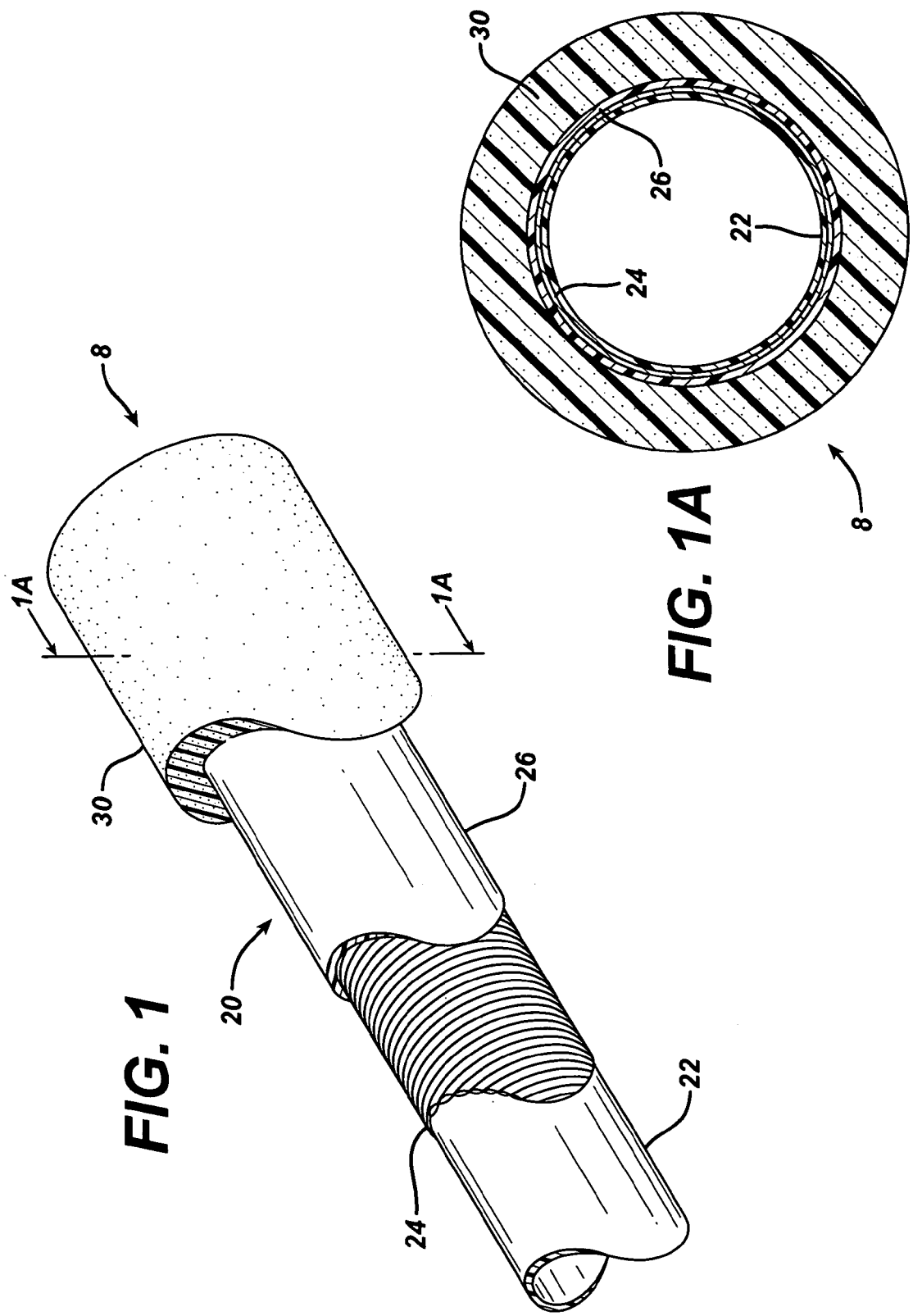
FIG. 1 is a perspective view of an anastomosis device of the present invention showing a graft coupling member coupled to an end of a tubular member.

Referring now to the drawings, and first to FIGS. 1 and 1A, an anastomosis device constructed according to the principles of the present invention is shown and generally indicated with reference numeral 8. The anastomosis device (or fastener) 8 is used to connect a graft vessel 10, such as a thoracic artery, to a target vessel 12, such as a coronary artery, i.e., the left anterior descending artery. For example, the device may be used in an end-to-side distal anastomosis to sealingly join a thoracic artery or a saphenous vein graft to a coronary artery. The anastomosis device 8 of the present invention may also be used in connecting various other vessels or arteries and may be used to connect synthetic vascular grafts to an artery.

The fastener 8 preferably comprises an elongated, flexible tubular member 20 and a radially compressible, elongated graft coupling member 30 which is coupled to an external surface of the tubular member 20 at one end of the tubular member 20. The graft coupling member 30 can be coupled to the tubular member 20 with biological glue, other adhesive means, thread, or by any other suitable means. Alternatively, the graft coupling member 30 and the tubular member 20 can also be provided as separate parts. The graft coupling member 30 will be configured to be stretched over one end of the tubular member 20 and secured proximal to the end of the tubular member 20 by the force of its own natural compressibility or by any of the coupling means described above.

The tubular member 20 comprises two tubular layers 22, 26, and a thin flexible central tube 24 interposed between the two tubular layers. The tubular layers are preferably formed from a biocompatible, implantable plastic material. The central tube 24 is preferably formed from a biocompatible coil such as medical grade stainless steel or nitinol wire or ribbon, but may also be formed from any other sufficiently rigid, biocompatible material such as a plastic, polyurethane or polycarbonate material, or any other suitable material as is well known to a person of ordinary skill in the art. The inner and outer tubular layers 22, 26 are preferably formed from a material having a low durometer hardness to provide sufficient flexibility to allow the tubular member to bend at an angle of approximately 30° to 60° along a central longitudinal axis of the member. Preferably, the inner and outer layers 22, 26 are made from an implantable, flexible plastic such as silicone, although any other suitable flexible, implantable biocompatible material as is well known to persons of ordinary skill in the art may be used. The inner and outer layers 22, 26 are preferably bonded together (similar to braided shafts) by conventional means and the central tube 24 is locked between two layers.

The inner plastic tube 22 is generally necessary to prevent the central coil 24 from scraping and damaging the graft vessel 10. The central coil 24 provides strength to the tubular member 20 to prevent it from kinking, yet is sufficiently flexible to allow the tubular member 20 to be inserted into the target vessel 12 through an incision 16 formed therein. The outer plastic tubular layer 26 allows the graft coupling member 30 to be more easily fitted over the tubular member 20 and coupled thereto. The tubular member 20 is preferably between about 4.0 and 12.0 mm in length, and more preferably about 5.0 to 8.0 mm, for example. As shown in FIG. 1, the inner and outer layers 22, 26 and central coil 24 preferably extend the full length of the tubular member 20. The diameter of the tubular member 20 will vary depending on the size of the graft vessel into which it is inserted. Preferably, the inner diameter of the inner layer 22 will generally be between about 0.5 to 6.0 mm for a coronary anastomosis, for example. The total wall thickness of tubular member 20 will be between about 0.100 mm and 0.600 mm, and preferably between about 0.100 mm and 0.400 mm, for example. It is to be understood, however, that other types of tubular members made from other types of biocompatible materials and different size tubular members may be used without departing from the scope of the invention. For example, the tubular member 20 may be formed from a one-piece flexible tube (not shown).

The graft coupling member (compressible portion) 30 comprises a tube formed from a biocompatible, radially compressible material. By "radially compressible", it is meant that the graft coupling member 30 is generally uniformly radially transformable between a free, normal expanded state and one or more compressed states in which the graft coupling member 30 has a smaller diameter than in its normal expanded state. In a preferred embodiment, the biocompatible material comprises a non-metallic foam material which is radially self-expandable. By "self-expandable", it is meant that the foam material forming the graft tubular member 30 is biased to its expanded state (i.e., will naturally tend to radially migrate back towards its free, normal expanded state from its compressed state). The coupling member 30 has an inner surface and an outer surface defining a wall thickness therebetween. The wall thickness of the coupling member in its compressed state is less than the wall thickness of the member in its expanded state. The foam material may be conventional biocompatible foam such as 100 pores per inch foam material, for example. The foam material is substantially radially compressible to allow the graft vessel 10 to be coupled to the foam and to permit the fastener 8 to move longitudinally within the target vessel 12 as will be described in greater detail below. The diameter of the graft coupling member 30 will vary depending on the size of the target vessel 12 into which the fastener 8 is inserted. Preferably, the inner diameter of the graft coupling member 30 will be about 10 to 30% smaller than the outside diameter of the tubular member 20, and the outside diameter of graft coupling member 30 will preferably be between about 10 to 80% larger than an inside diameter of the target vessel 12.

FIGS. 2–9 show an exemplary use of the anastomosis device 8 of the present invention in an open surgical coronary artery bypass graft procedure via a median sternotomy. This example is meant to be by illustration only, and in no way is meant to be limiting. The present invention can be used in other cardiac surgery procedures such as minimally invasive direct coronary artery bypass grafting (MID-CAB) on a beating heart through a small incision (thoracotomy) (about 6–8 cm) in the left side of the chest wall, in endoscopic minimally invasive cardiac surgery bypass graft procedures, and in other vascular procedures to join two vessels together. By way of example, the left internal thoracic artery is used as the graft vessel 10. In this example, the left anterior descending artery is used as the target vessel 12 and contains a build-up of plaque or narrowing 13. If left untreated, this diseased artery may lead to insufficient blood flow and eventual angina, ischemia, and possibly myocardial infarction.

Conventional coronary bypass graft procedures require that a source of arterial blood be prepared for subsequent bypass connection to the diseased artery. An arterial graft can be used to provide a source of blood flow, or a free vessel graft may be used and connected at the proximal end to a source of blood flow. Preferably, the source of blood flow is any one of a number of existing arteries that are dissected in preparation for the bypass graft procedure. In many instances, it is preferred to use either the left or right internal thoracic artery. In multiple bypass procedures, it may be necessary to use free graft vessels such as the saphenous vein, gastroepiploic artery in the abdomen, and other arteries harvested from the patient's body as well as synthetic graft materials, such as Dacron or Gortex grafts. If a free graft vessel is used, the upstream end (proximal) of the dissected vessel, which is the arterial blood source, will be secured to the aorta to provide the desired bypass blood flow, and the downstream end (distal) of the dissected vessel will be connected to the target vessel in a distal anastomosis.

Figure 2:
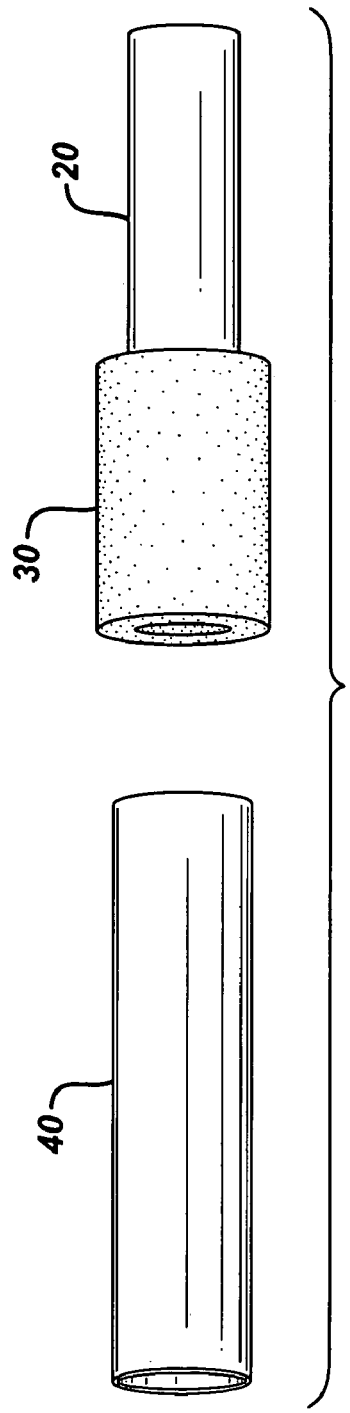
FIG. 2 shows the anastomosis device of FIG. 1 prior to insertion of the device into an opening in an introducer.
Figure 3:
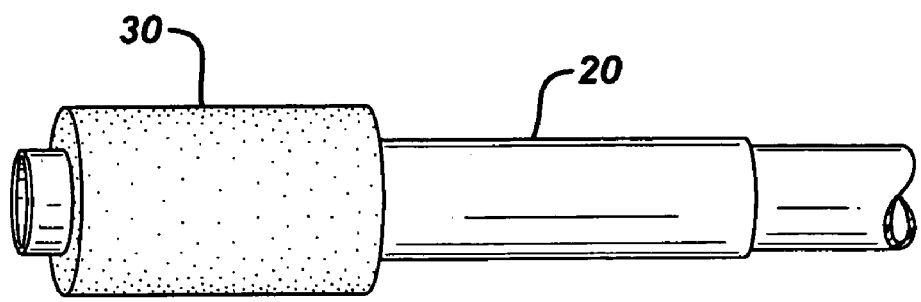
FIG. 3 is an elevated view of the anastomosis device of FIG. 2 with a free end of a graft vessel inserted therein.
Figure 4:
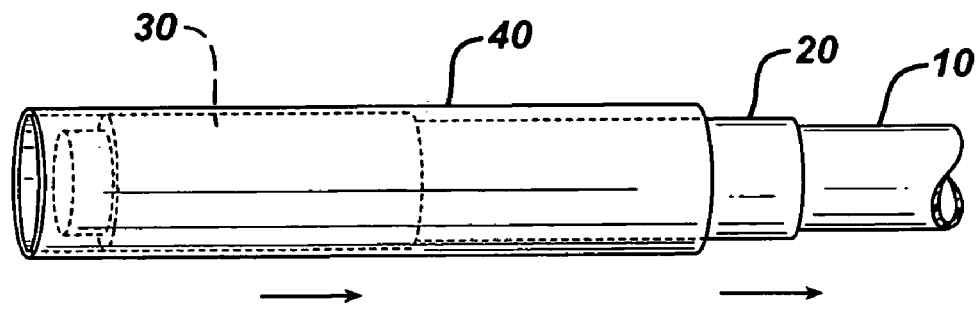
FIG. 4 is an elevated view of the anastomosis device of FIG. 3 with the device inserted into the introducer showing the graft coupling member in a compressed state within the introducer.
Figure 5:
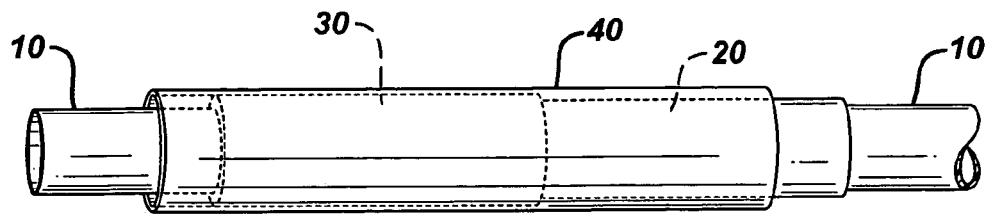
FIG. 5 is an elevated view of the anastomosis device of FIG. 4 with the free end of the graft vessel shown extending longitudinally from an end of the introducer.
Figure 6:
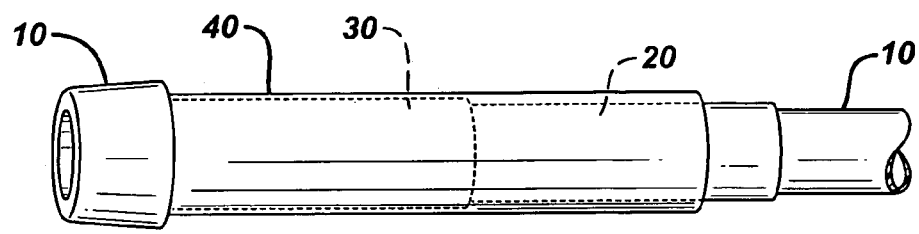
FIG. 6 is an elevated view of the anastomosis device of FIG. 5 with the free end of the graft vessel everted over an end of the introducer.
Figure 7:
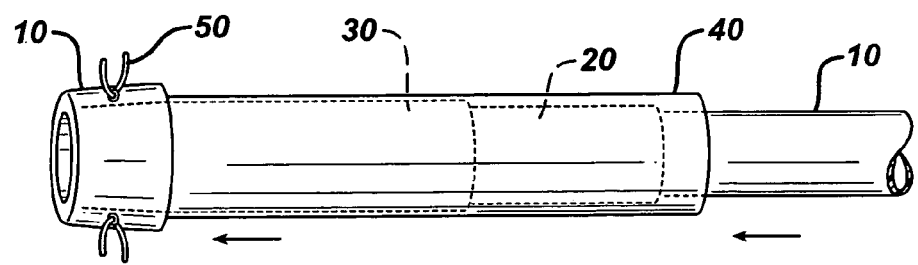
FIG. 7 is an elevated view of the anastomosis device of FIG. 6 showing a portion of the graft coupling member extending longitudinally from an end of the introducer and showing the application of one or more sutures between the everted graft vessel and the graft coupling member.

In order to perform an anastomosis with the fastener 8 of the present invention, the graft vessel 10 is first coupled to the fastener 8 by inserting a free end of the graft vessel 10 through an opening in the tubular member 20 with a conventional insertion device (not shown) and moving the graft vessel 10 longitudinally within the tubular member 20 until the free end of the graft vessel extends a short distance beyond an end of the tubular member as shown in FIG. 3. The fastener 8 with the graft coupling member 30 attached thereto is then inserted into an opening in a tubular introducer 40 which has an inner diameter smaller than an outside diameter of the graft coupling member 30 but larger than an outside diameter of the flexible tubular member 20 (FIG. 2). The introducer 40 preferably includes at least one longitudinal perforation (not shown) to allow for easy removal of the introducer as further described below. The inner wall of the introducer 40 will radially compress the graft coupling member 30 into its at least one compressed state. The free end of the graft vessel 10 is then everted over an end of the introducer 40 as shown in FIG. 6. The introducer 40 is then pulled back to a short distance over the fastener 8 (while holding tubular member 20) to a position in which at least an end portion of the graft coupling member 30 is exposed and extends a short distance from an end of the introducer 40 and engages with a portion of the graft vessel 10 in the everted configuration (FIG. 7). The natural adhesiveness of graft vessel 10 may be sufficient to secure the graft vessel 10 to the graft coupling member 30. If necessary, one or more sutures 50 may be applied to the graft vessel 10 and the graft coupling member 30 to secure the graft vessel 10 to the fastener 8 in the event that the natural adhesiveness and compressibility of the graft vessel 10 is insufficient to temporarily secure it to the graft coupling member 30. Alternatively, the graft vessel 10 can be secured to the graft coupling member 30 with biological glue, other adhesive means, by tying one or more sutures circumferentially around the graft vessel 10, or by any other suitable means.

Figure 2A:
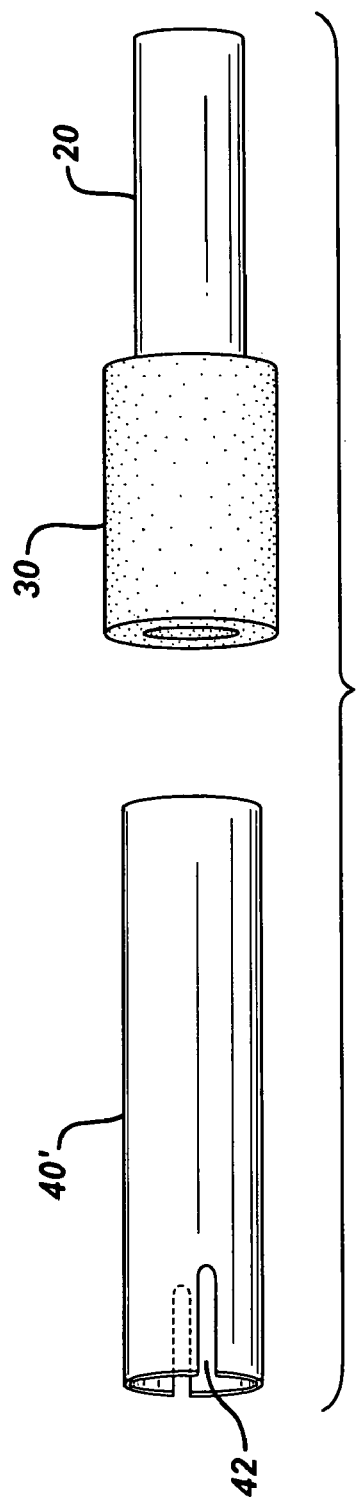
FIG. 2A shows the anastomosis device of FIG. 1 prior to insertion of the device into an opening in an alternative embodiment of the introducer of FIG. 2.
Figure 7A:
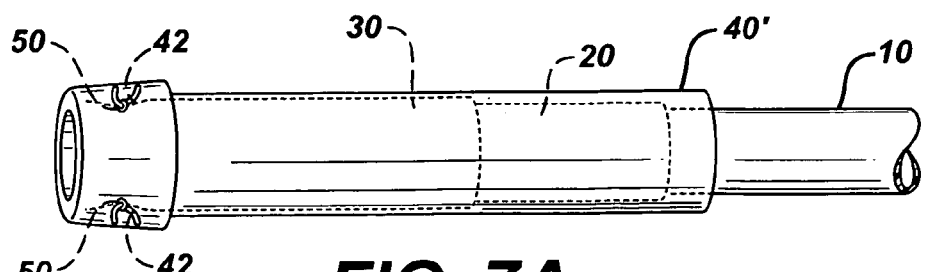
FIG. 7A is an elevated view of the anastomosis device of FIG. 1 shown inserted into the introducer of FIG. 2A.

An alternative embodiment of the tubular introducer 40' is shown in FIGS. 2A and 7A. The introducer includes at least one groove 42 formed in one end of the wall of the introducer. One or more sutures 50 can be inserted through the groove 42 to secure the everted graft vessel 10 to the graft coupling member 30. It is to be understood that the introducer may have configurations other than those shown herein without departing from the scope of the invention.

Figure 8:
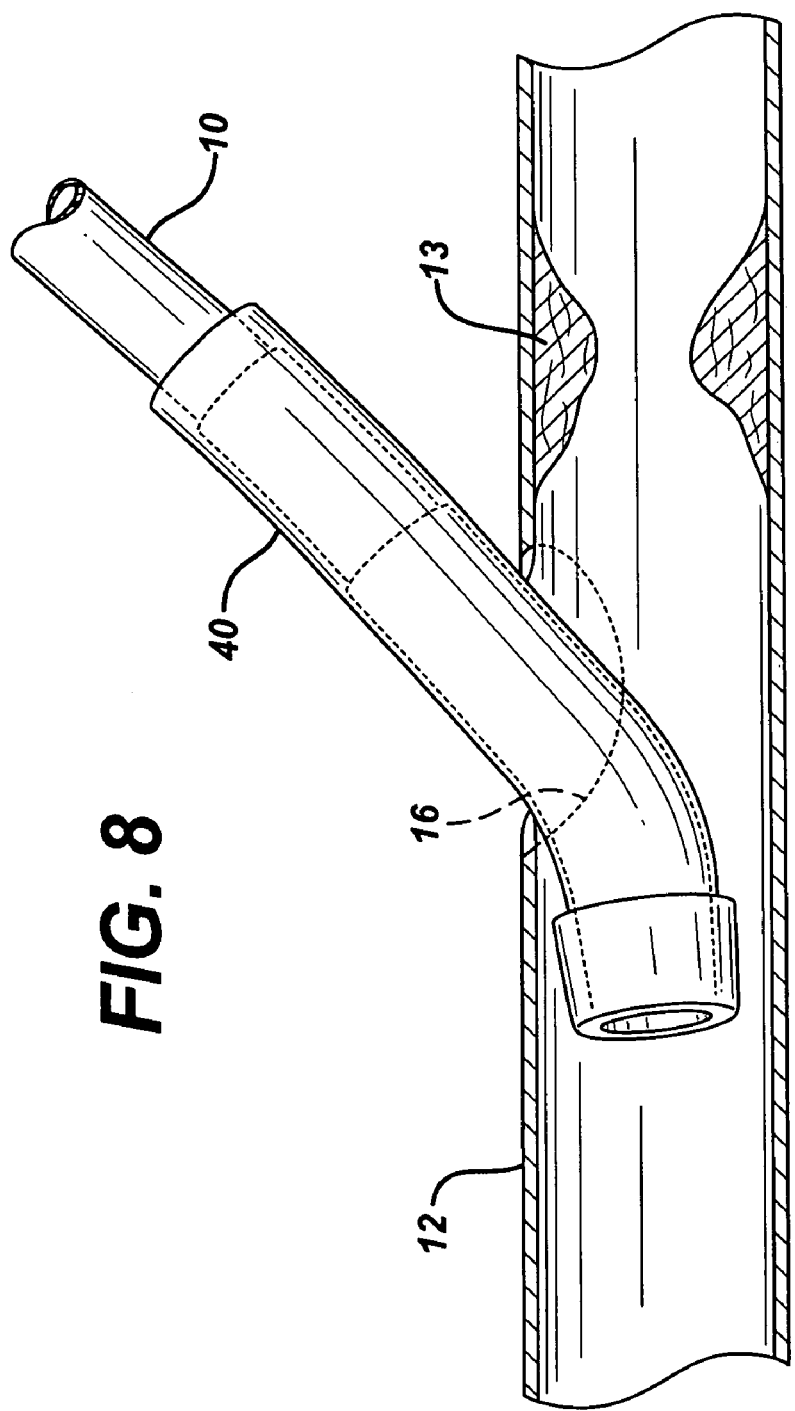
FIG. 8 is an elevated view of the anastomosis device of FIG. 7 inserted into a target vessel through an incision in the target vessel.

The introducer (40 or 40') is then introduced into the target vessel 12 through an incision (opening) 16 formed in a side wall of the target vessel 12 (FIG. 8). The incision 16 can be made with the use of a conventional scalpel or other appropriate cutting instrument. Alternatively, a circular or oval punch may be used to facilitate the arteriotomy. The fastener 8 is preferably positioned in the target vessel 12 via introducer 40, 40' such that at least an end portion of the graft coupling member 30 extends generally coaxial with the target vessel 12. With the fastener 8 securely positioned in the target vessel 12 via the introducer 40, 40', the introducer can be pulled back over the fastener to allow the graft coupling member 30 to radially expand back towards its normal expanded state to sealingly engage the fastener with an inner wall of the target vessel to complete the anastomosis. The introducer 40, 40' preferably will be a conventional peel-away introducer such as that manufactured by Modified Polymer Components, Inc. of Sunnyvale, Calif., so that it can be easily separated and removed from the fastener 8 and graft vessel 10.

Figure 9:
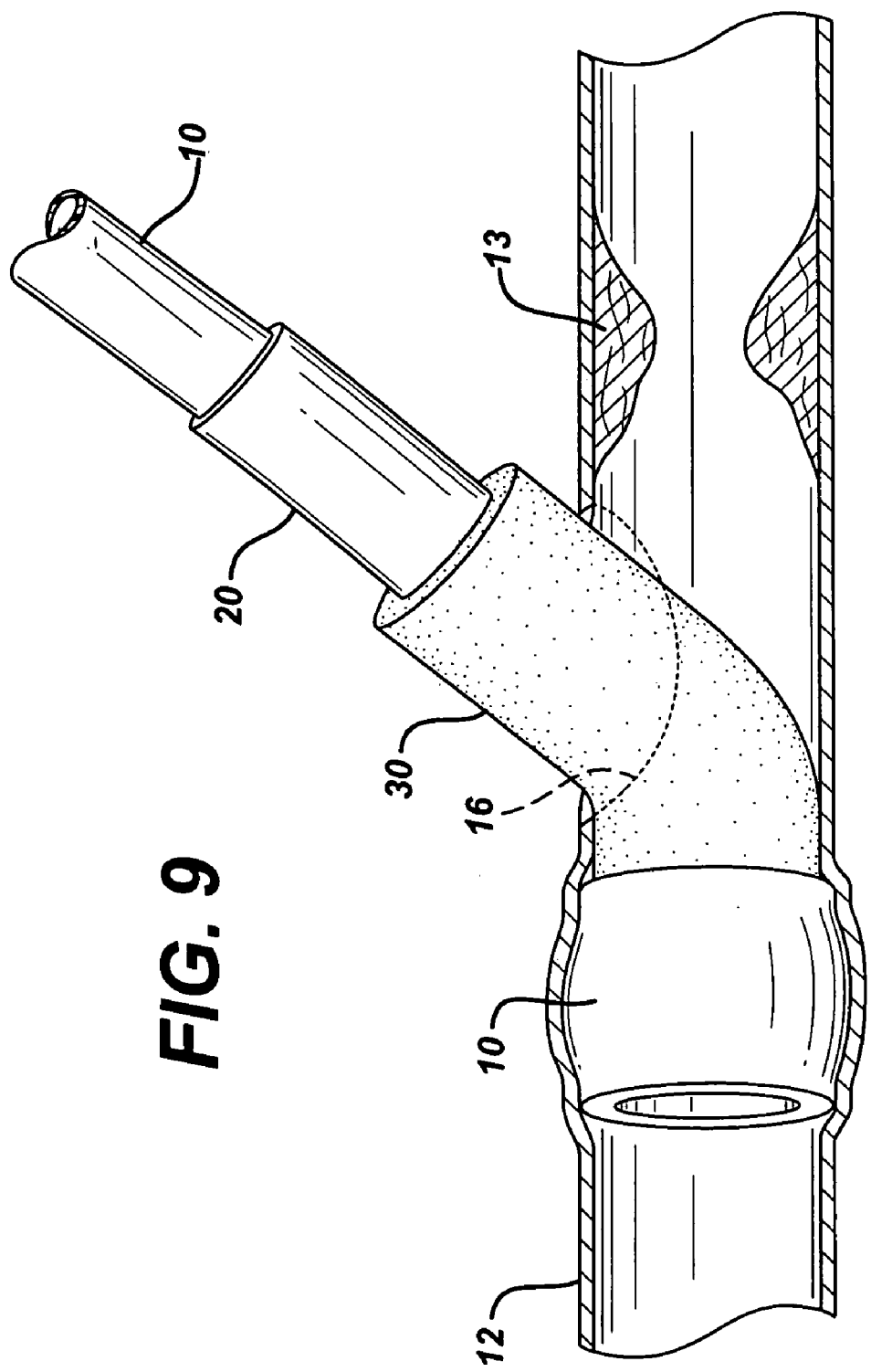
FIG. 9 is an elevated view of the anastomosis device of FIG. 8 after the introducer has been removed from the fastener showing the completed anastomosis.

As shown in FIG. 9, the self-expanding nature of the graft coupling member 30 permits the graft coupling member 30 to radially expand to sealingly engage the graft vessel 10 with an inner wall of the target vessel 12 to complete the anastomosis. The engagement of the fastener 8 with the graft vessel 10 and inner wall of the target vessel 12 prevents substantial longitudinal movement of the fastener 8 within the target vessel. If necessary, one or more sutures can be applied to the anastomosis site to prevent the graft vessel 10 from being pulled out from the target vessel 12. The foam material forming the graft coupling member 30 will apply a gentle circumferentially uniform, radial pressure against the inverted graft vessel 10 and the inner wall of the target vessel 12. An intima-to-intima anastomosis results. The flexibility of the foam material and the tubular member 20 permits the fastener device 8 to be substantially compliant with the target vessel 12 and the graft vessel 10 to reduce the onset of thrombosis.

If required, cardiac stabilization such as described in co-pending provisional patent application Ser. No. 60/055,127, for Compositions, Apparatus and Methods For Facilitating Surgical Procedures, filed Aug. 8, 1997 and invented by Francis G. Duhaylongsod, M.D, may be used during the procedure. Other pharmacological or mechanical methods may also be used.

In an alternative embodiment of the present invention shown in FIG. 10, wherein like numerals represent like parts, the fastener 60 shown therein comprises a single, elongated tubular member 70 made from a radially compressible and radially self-expandable material, preferably a non-metallic foam material. The foam material is preferably sufficiently radially rigid to maintain its shape within the target vessel 12 to provide a fluid-tight seal, and should also be sufficiently flexible to be inserted through an incision 16 in the target vessel 12. The foam material in this embodiment is preferably foam such as manufactured by W. L. Gore of Arizona, for example. Alternatively, the foam may be a material having 100 pores per inch as described above. The outer diameter of the tubular member 70 in its free expanded state is preferably between about 10 to 80% larger than the inner diameter of the target vessel 12 into which it is inserted, and the inner diameter of the tubular member 70 in its free expanded state is preferably about 10% to 30% larger than the outer diameter of the graft vessel 10. The tubular member 70 is preferably between about 4.0 and 12.0 mm in length, and more preferably about 5.0 to 8.0 mm in length, for example.

Figure 12:
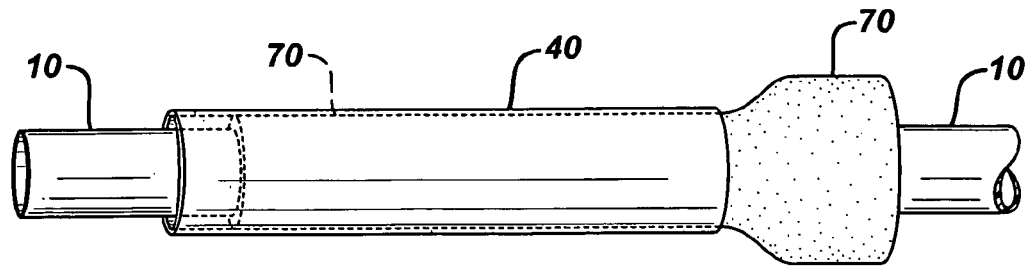
FIG. 12 is an elevated view of the anastomosis device of FIG. 11 with the device inserted into the introducer and showing the tubular member in a compressed state within the introducer.
Figure 13:
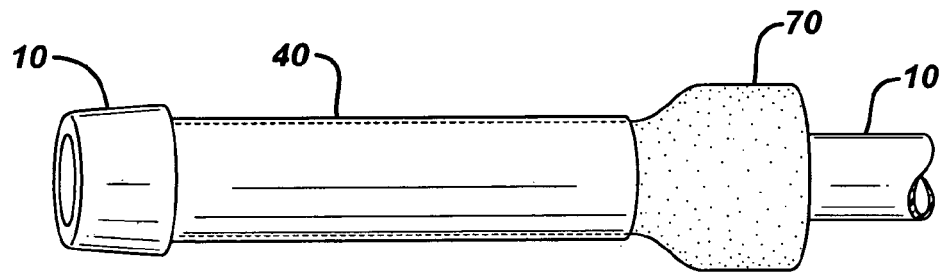
FIG. 13 is an elevated view of the anastomosis device of FIG. 12 with the free end of the graft vessel everted over an end of the introducer.
Figure 14:
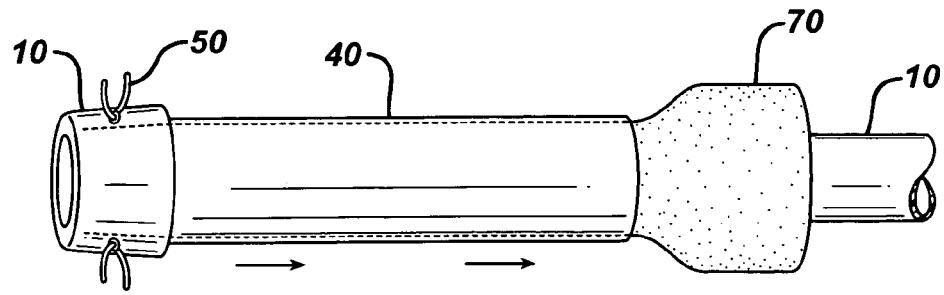
FIG. 14 is an elevated view of the anastomosis device of FIG. 13 showing a portion of the tubular member extending longitudinally from an end of the introducer and showing the application of one or more sutures between the exerted graft vessel and the tubular member.

The graft vessel 10 may be coupled to the tubular member 70 and inserted into the target vessel 12 in substantially the same way as described above for the tubular member/graft coupling member combination of FIGS. 1-9. Referring to FIGS. 11-16, the foam tubular member 70 and graft vessel 10 is inserted into an opening in a tubular introducer 40 which has an inner diameter which is smaller than an outside diameter of the tubular member 70, as shown in FIG. 11. The inner wall of the introducer 40 will radially compress the tubular member 70 into a compressed state. A free end of the graft vessel 10 is then inserted through an opening in the tubular member 70 and everted over an end of the introducer 40 (FIGS. 12 and 13). The introducer 40 can then be pulled back a short distance over the tubular member 70 (while holding tubular member 70) to a position in which at least an end portion of the tubular member 70 is exposed and extends a short distance from an end of the introducer 40 and engages a portion of the graft vessel 10 in the everted configuration (FIG. 14). One or more sutures 50 may be applied between the graft vessel 10 and the tubular member 70 to secure the graft vessel 10 to the tubular member 70. Alternatively, the graft vessel 10 may be secured to the tubular member 70 with biological glue, other adhesive means, by tying one or more sutures circumferentially around the graft vessel 10, or by any other suitable means.

Figure 15:
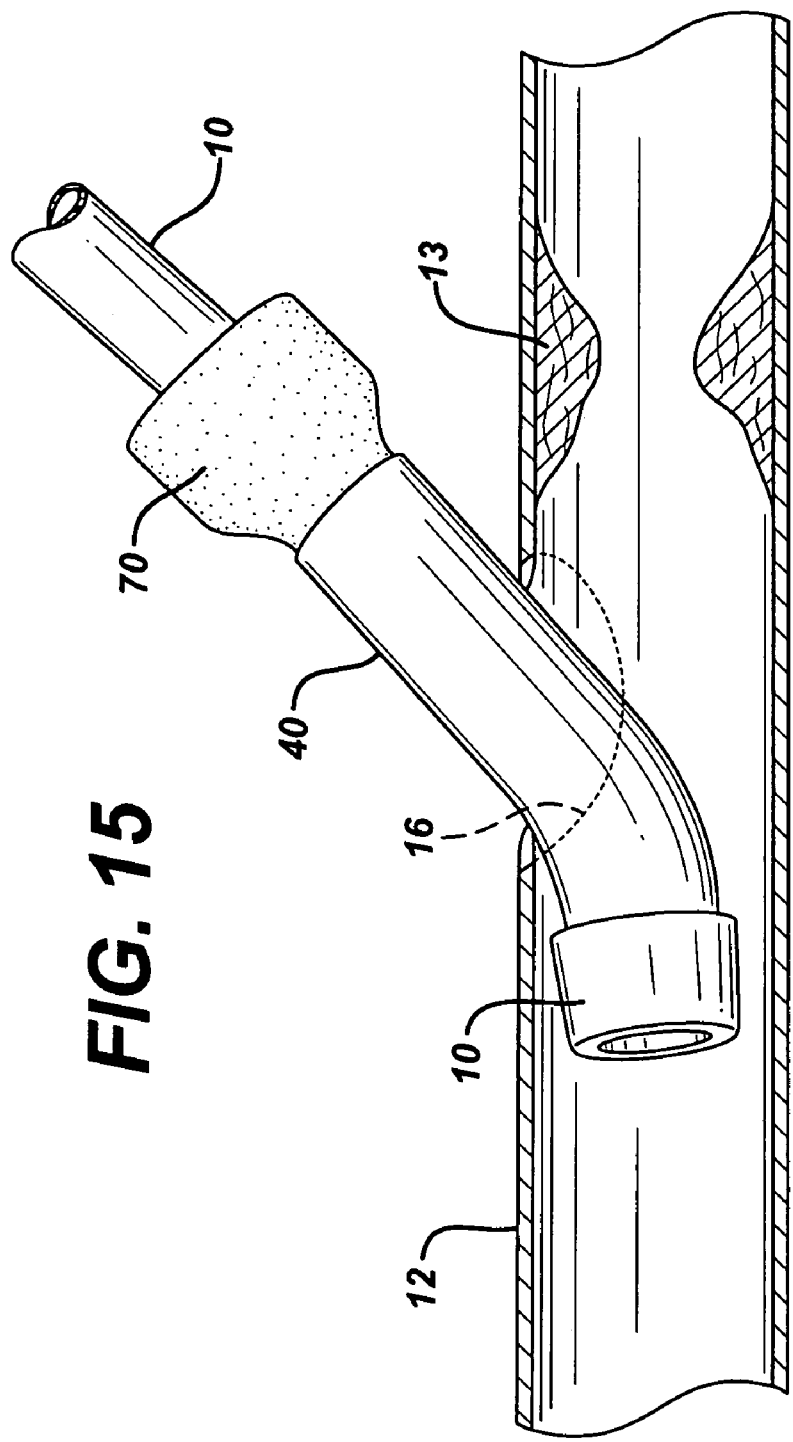
FIG. 15 is an elevated view of the anastomosis device of FIG. 14 inserted into the target vessel through an incision in the target vessel.
Figure 16:
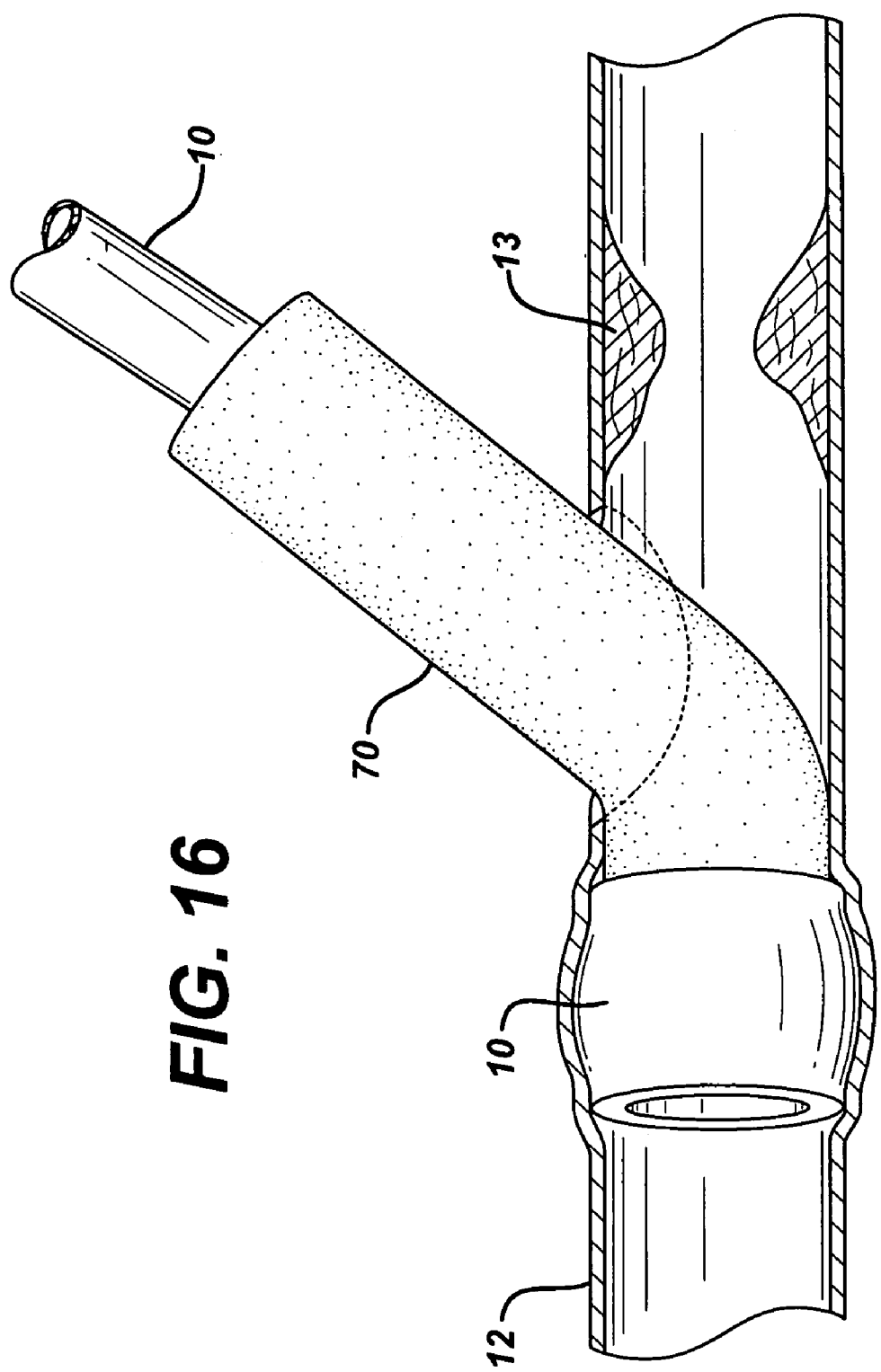
FIG. 16 is an elevated view of the anastomosis device of FIG. 15 after the introducer has been removed from the fastener showing the completed anastomosis.

Alternatively, the tubular member 70 may be coupled to the graft vessel 10 by providing an introducer (not shown) as described above with reference to FIG. 7A having at least one groove in a wall of the introducer which extends axially from an end of the introducer. One or more sutures can be provided through the groove to secure the everted graft vessel 10 to the tubular member 70. The introducer 40 is then introduced into the target vessel 12 through an incision 16 in a wall of the target vessel 12 and pulled back over the tubular member 70 (FIG. 15). The tubular member 70 will then radially expand back towards its free, normally expanded state to sealingly join the graft vessel 10 to the target vessel 12 in a compliant, patent anastomosis (FIG. 16). If necessary, one or more stay sutures can be applied to the anastomosis site to prevent the graft vessel 10 from pulling out the target vessel 12. The introducer 40 can then be peeled away from the tubular member 70 and the graft vessel 10 to complete the anastomosis procedure.

While the above is a complete description of the preferred devices and methods of the invention, various alternatives, substitutions, modifications, and equivalents of the devices and methods described are possible without departing from the principles thereof. For example, it may be possible for a surgeon to radially compress the graft coupling member with his fingers or other appropriate surgical instrument without requiring the use of a separate tubular introducer. The surgeon can then deftly evert the graft vessel over the compressed graft coupling member (or one-piece tubular member) to couple them to one another. The surgeon can then use his fingers to continue to radially compress the graft coupling member as it is inserted into the target vessel through an incision formed therein. By removing his fingers from engagement with the graft coupling member, the graft coupling member will tend to radially expand back towards its normal expanded state to sealingly engage the graft vessel with an inner wall of the target vessel in a completed anastomosis. Similarly, other alternatives, substitutions, modifications and equivalents are possible without departing from the scope of the inventions described herein. Therefore, nothing disclosed above should be taken to limit the scope of the invention, which is defined by the appended claims.

All references cited herein are incorporated by reference.

What is claimed is:

1. An anastomosis device for use in coupling a graft vessel to a side of a target vessel, the target vessel having an opening formed in a side wail thereof, the anastomosis device comprising:
   a graft vessel having an end portion and a proximal portion;
   a coupling member attached to the graft vessel:
   a flexible tube attached to the coupling member: and
   wherein the graft vessel extends through the flexible tube, a free end of the graft vessel is evened over and coupled to at least a portion of the coupling member, the coupling member is radially compressible to a compressed state for insertion of at least a portion of the coupling member and at least a portion of the end portion of the graft vessel into the opening of the target vessel, and the coupling member is positionable within the opening of the target vessel when the coupling member expands from the compressed state to an expanded state.

2. The device of claim 1 wherein said coupling member is self-expanding.

3. The device of claim 1, wherein said flexible tube is made from an implantable biocompatible material.

4. The device of claim 3 wherein said biocompatible material comprises a plastic material.

5. The device of claim 1, wherein the flexible tube further comprises a coil interposed between an inner and outer layer.

6. The device of claim 5 wherein said coil is formed from a biocompatible material.

7. The device of claim 6 wherein said biocompatible material is selected from a group consisting of stainless steel and nitinol.

8. The device of claim 6 wherein said biocompatible material is selected from a group consisting of plastic, polyurethane, and polycarbonate material.

9. The device of claim 5 wherein said inner and outer layers are formed from a low durometer plastic material.

10. The device of claim 9 wherein said plastic material is silicone.

11. The device of claim 1 wherein said coupling member is made from a biocompatible material.

12. The device of claim 11 wherein said biocompatible material comprises a non-metallic material.

13. The device of claim 12 wherein said non-metallic material comprises a foam material.

14. The device of claim 1 wherein an outside diameter of the coupling member in its expanded state is between about 10 to 80 percent larger than an inside diameter of the target vessel.

15. The device of claim 1 wherein an inside diameter of the flexible tube is between about 0.5 mm to 6.0 mm.

16. The device of claim 1, wherein the graft vessel is coupled to the coupling member with one or more sutures.

17. The device of claim 1 further comprising an introducer having an outer diameter sized to permit insertion of the introducer through the opening in the side wall of the target vessel.

18. The device of claim 17, wherein the introducer has a groove farmed in one end thereof through which a suture can be attached to the graft vessel and the flexible tube.

19. The device of claim 18 wherein the introducer is configured to be pulled back and separated from the flexible tube after the introducer is inserted at least partially into the target vessel through the opening in the side wall of the target vessel.

20. The device of claim 1, wherein the graft vessel comprises one of an artery, a vein, and a synthetic graft.

21. An anastomosis device for use in coupling a graft vessel to a side of a target vessel, the target vessel having an opening formed in a side wall thereof, the anastomosis device comprising:
   a graft vessel having an end portion and a proximal portion;
   a coupling member attached to the graft vessel;
   a flexible tube at least partially disposed about the graft vessel and attached to the coupling member; and
   wherein a free end of the graft vessel is evened over and coupled to at least a portion of the coupling member, the coupling member is radially compressible to a compressed state for insertion of at least a portion of the coupling member and at least a portion of the end portion of the graft vessel into the opening of the target vessel, and the coupling member is positionable within the opening of the target vessel when the coupling member expands from the compressed state to an expanded state.

* * * * *